(12) United States Patent
Itoh (10) Patent No.: US 10,183,817 B2
(45) Date of Patent: Jan. 22, 2019

(54) CONTAINER COLLECTING DEVICE AND URINALYSIS APPARATUS USING CONTAINER COLLECTING DEVICE

(71) Applicant: IDS CO., LTD., Kumamoto-shi, Kumamoto (JP)

(72) Inventor: Teruaki Itoh, Kumamoto (JP)

(73) Assignee: IDS Co., Ltd., Kumamoto (JP)

( * ) Notice: Subject to any disclaimer, the term of this patent is extended or adjusted under 35 U.S.C. 154(b) by 126 days.

(21) Appl. No.: 14/682,688

(22) Filed: Apr. 9, 2015

(65) Prior Publication Data

US 2015/0307293 A1 Oct. 29, 2015

(30) Foreign Application Priority Data

Apr. 24, 2014 (JP) ................. 2014-090584

(51) Int. Cl.
  *B65G 57/16* (2006.01)
  *A61B 10/00* (2006.01)
  *B65B 35/50* (2006.01)
  *G01N 35/00* (2006.01)

(52) U.S. Cl.
  CPC .......... *B65G 57/165* (2013.01); *A61B 10/007* (2013.01); *B65B 35/50* (2013.01); *G01N 35/0099* (2013.01); *G01N 2035/00178* (2013.01); *G01N 2035/00277* (2013.01)

(58) Field of Classification Search
  CPC ..... B65G 57/165; A61B 10/007; B65B 35/50; G01N 35/0099; G01N 2035/00178
  USPC .......................................... 414/788.2; 53/437
  See application file for complete search history.

(56) References Cited

U.S. PATENT DOCUMENTS

| 2,736,149 | A | * | 2/1956 | Earp | ................... | B65G 57/165 |
|---|---|---|---|---|---|---|
| | | | | | | 198/597 |
| 3,685,671 | A | | 8/1972 | Layman | | |
| 3,805,482 | A | * | 4/1974 | O'Shea | ................ | B65B 25/145 |
| | | | | | | 53/120 |
| 4,545,714 | A | * | 10/1985 | Johnson | ................ | B65G 51/02 |
| | | | | | | 198/623 |
| 5,484,254 | A | * | 1/1996 | Schiffelholz | .......... | G07F 7/0609 |
| | | | | | | 193/47 |

(Continued)

FOREIGN PATENT DOCUMENTS

| CN | 1919707 | 2/2007 |
|---|---|---|
| GB | 232881 | 4/1925 |

(Continued)

OTHER PUBLICATIONS

Taiwanese Patent Office, "Office Action and Search Report," issued in connection with Taiwanese Patent Application No. 104111954, dated Feb. 22, 2016, with partial English translation.

(Continued)

*Primary Examiner* — Lynn E Schwenning
(74) *Attorney, Agent, or Firm* — Nixon & Vanderhye P.C.

(57) ABSTRACT

A container collecting device which stacks and collects containers each formed by closing a small-diameter side of a tapered cylinder. The container collecting device comprises that a guide cylinder having an inner diameter larger than the largest outer diameter of the container and extending in a gravity direction, and a supporter that supports the container at a lower end of the guide cylinder; and an actuator to move the container.

2 Claims, 7 Drawing Sheets

(56) References Cited

U.S. PATENT DOCUMENTS

| | | | | |
|---|---|---|---|---|
| 5,888,046 A | * | 3/1999 | Salda | G07F 7/0609 |
| | | | | 194/205 |
| 6,053,695 A | * | 4/2000 | Longoria | A21C 9/086 |
| | | | | 414/788.9 |
| 2006/0219610 A1 | | 10/2006 | Varney et al. | |
| 2011/0076127 A1 | * | 3/2011 | Berg | B65G 57/165 |
| | | | | 414/788.2 |
| 2013/0205723 A1 | * | 8/2013 | Blake | G07F 9/08 |
| | | | | 53/473 |
| 2013/0283731 A1 | * | 10/2013 | Komp | B65B 5/06 |
| | | | | 53/268 |

FOREIGN PATENT DOCUMENTS

| | | | | |
|---|---|---|---|---|
| JP | 58-109323 | | 6/1983 | |
| JP | 2-117501 | | 5/1990 | |
| JP | 6-92463 | | 4/1994 | |
| JP | 10-142235 | | 5/1998 | |
| JP | H 10142235 | * | 5/1998 | B65C 3/12 |
| JP | 2000-53205 | | 2/2000 | |
| JP | 3197628 | | 8/2001 | |
| JP | 2002-104601 | | 4/2002 | |
| JP | 2010-155713 | | 7/2010 | |
| KR | 0132655 | * | 4/1998 | B65G 9/06 |

OTHER PUBLICATIONS

Canadian Office Action issued in Application No. 2,888,401 dated Apr. 4, 2016.
Korean Office Action issued in App. No. 10-2015-0056344 dated Mar. 25, 2016 (w/ partial trans.).
Chinese Office Action issued in App. No. 201510197326.2 dated May 30, 2016 (w/ partial trans.).
Extended European Search Report issued in EP Application No. 15001158.3 dated Aug. 14, 2015.
Chinese Office Action issued in App. No. 201510197326.2 dated Feb. 17, 2017 (w/ translation).
Japanese Office Action issued in Appln. No. 2014-090584 dated Dec. 5, 2017 (w/ translation).
Office Action issued in JP Appln. No. 2014-090584 dated Jul. 3, 2018 (w/ translation).

* cited by examiner

CONTAINER COLLECTING DEVICE AND URINALYSIS APPARATUS USING CONTAINER COLLECTING DEVICE

CROSS-REFERENCE TO RELATED APPLICATION

This application is based upon and claims the benefit of priority from Japanese Patent Application No. 2014-090584, filed Apr. 24, 2014, the entire contents of which are incorporated herein by reference.

BACKGROUND OF THE INVENTION

An embodiment of the invention relates to a container collecting device and a urinalysis apparatus in which the container collecting device is used.

Usually, in a urinalysis, tapered cylindrical paper containers are used. The end portion on the small-diameter side of each paper container is closed. After urine sampling, the paper containers are collected and discarded. In recent years, a collecting device has been developed which automatically collects the paper containers (Jpn. Pat. Appln. KOKAI Publication No. 2010-155713).

This collecting device has a cylindrical guide having an inner diameter larger than the largest diameter of the paper containers. The cylindrical guide is extended in a perpendicular direction and the paper container is inserted into the cylinder from an upper end of the guide. The paper container is inserted into the cylindrical guide from the small-diameter side of the container to be stacked in the vicinity of a lower end of the cylindrical guide.

When the paper container is inserted into the cylindrical guide and the paper container is tilted or wet, the paper container sometimes gets hung up and does not stack properly. In this case, only a number of the paper containers smaller than a pre-determined number can be received, with the result that this cylindrical guide, i.e., the guide cylinder, quickly becomes full. Every time the guide cylinder becomes full, it is necessary to remove the paper containers from the collecting device. Therefore, the number of times to remove the paper containers from the guide cylinder increases.

BRIEF SUMMARY OF THE INVENTION

A container collecting device which stacks and collects containers each formed by closing a small-diameter side of a tapered cylinder. The container collecting device comprises that a guide cylinder having an inner diameter larger than the largest outer diameter of the container and extending in a gravity direction, and a supporter that supports the container at a lower end of the guide cylinder; and an actuator to move the container.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinafter, a first embodiment of the present invention will be described with reference to the drawings.

Figure 1:
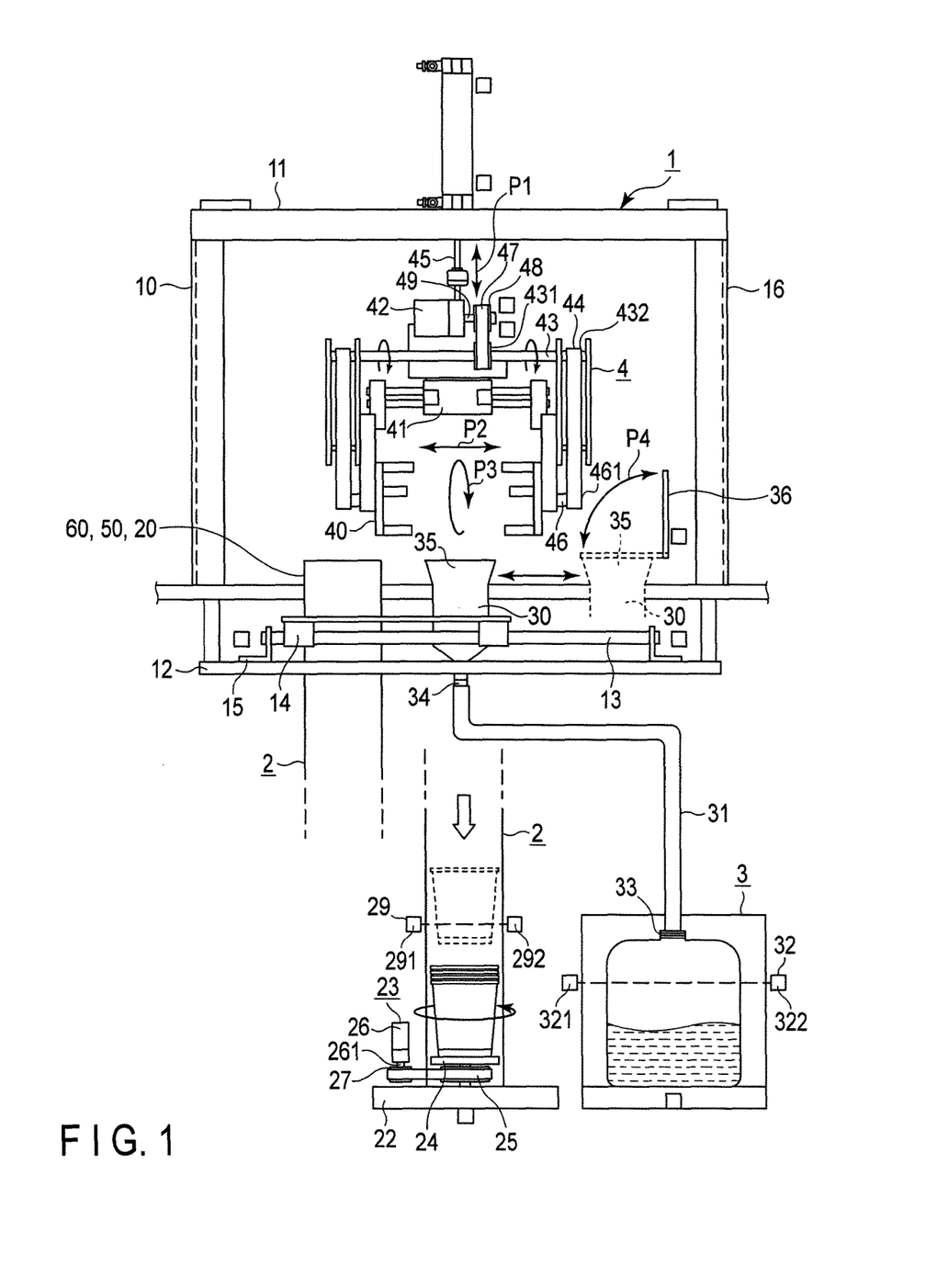
FIG. 1 is a schematic view of a main part of a urinalysis apparatus comprising a container collecting device of a first embodiment.

FIG. 1 shows a main part of a urinalysis apparatus 1 that analyzes a patient's urine sampled in each container during urinalysis performed in a hospital, a medical institution, or the like. In particular, FIG. 1 mainly shows a waste liquid tank 3 into which the urine left in the container is discarded, and a container collecting device 2. The containers for use in the urinalysis have the same shape.

The urinalysis apparatus 1 of the first embodiment includes a case 10, the container collecting device 2, the waste liquid tank 3, an arm 4, and a control section 100 that controls these devices.

The case 10 includes a ceiling portion 11 that supports the arm 4, a bottom portion 12 in which the container collecting device 2 and a rotor 30 of the waste liquid tank 3 are disposed, and a side wall 16.

In the case 10, the arm 4 is hung from the ceiling portion 11.

The arm 4 includes a lifting mechanism 45 and a gripping portion 40. The lifting mechanism 45 moves the arm 4 in an upward-downward direction as shown by an arrow P1. In addition, the gripping portion 40 is opened and closed as shown by an arrow P2, and is rotated around a rotary shaft 46 as shown by an arrow P3. That is, when a motor 42 rotates, a rotating force is transmitted to the gripping portion 40 via a rotary shaft 49, a pulley 48, an endless belt 47, a pulley 431, a drive shaft 43, a pulley 432, an endless belt 44, a pulley 461, and the rotary shaft 46. This enables an operation of tilting the container to a predetermined angle.

In the bottom portion 12, the container collecting device 2 and the rotor 30 communicating with the waste liquid tank 3 are disposed. The container collecting device 2 and the rotor 30 are combined by a fixing fence 14, and attached slidably along a rail 13. The rail 13 is fixed to the bottom portion 12 by a fixing tool 15. The container collecting device 2 and the rotor 30 are attached via a predetermined space so that when the rotor 30 is present at a position of a lid 36, the container collecting device 2 comes under the arm 4. Additionally, in a region of the bottom portion 12 which faces the rail 13, an opening (not shown) is disposed to acquire a moving path of the container collecting device 2 and the rotor 30.

The waste liquid tank 3 is a tank that collects the urine left after the urinalysis. In the waste liquid tank 3, a sensor 32 is disposed that detects an amount of a waste liquid that reaches such an amount as to fill up the tank. A so-called optical sensor, for example, can be used as the sensor 32. Specifically, when an optical axis extending from a light emitting portion 321 toward a light receiving portion 322 is blocked by a material or a liquid, a quantity of light to be received by the light receiving portion 322 changes. The sensor 32 detects the change of the quantity of the light to be received by the light receiving portion 322, and detects that a level of the collected waste liquid has reached a predetermined amount.

In addition, an opening 33 of an upper portion of the waste liquid tank 3 is coupled with a flexible waste liquid tube 31. One end of the waste liquid tube 31 is coupled with the opening 33 of the waste liquid tank 3, and the other end thereof is coupled with a lower end portion 34 of the rotor 30.

In the first embodiment, a so-called disposable paper container is used as the container. Note that a material of the container is not limited to paper as long as the container has a tapered shape and can be stacked and collected.

The container collecting device 2 is disposed adjacent to the left of the waste liquid tank 3 as shown in the drawing. Note that in FIG. 1 the container collecting device 2 is divided and depicted in two parts for convenience to show a moving range of the container collecting device 2, but the device is actually one device.

Figure 2:
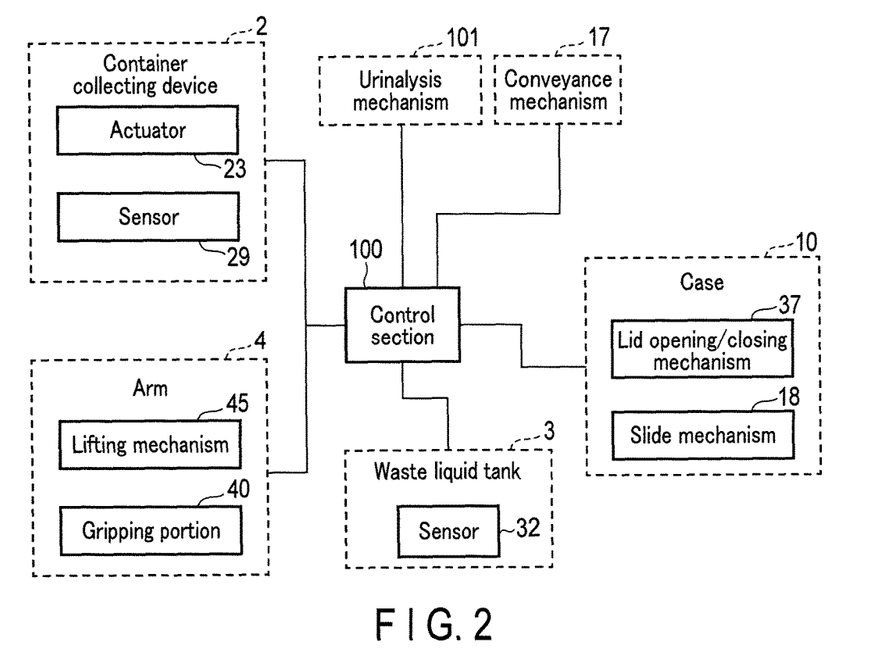
FIG. 2 is a block diagram showing a control system of the urinalysis apparatus of FIG. 1.

As shown in FIG. 2, operations of respective parts of the urinalysis apparatus 1 are controlled by the control section 100. Specifically, the control section 100 controls a conveyance mechanism 17, a urinalysis mechanism 101, an actuator 23 and a sensor 29 of the container collecting device 2, the lifting mechanism 45 and the gripping portion 40 of the arm 4, the sensor 32 of the waste liquid tank 3, a lid opening/closing mechanism 37 that opens and closes the lid 36, and a slide mechanism 18 that slides the fixing fence 14 along the rail 13.

Next, the operation of the urinalysis apparatus 1 of the above structure will be described.

Prior to the operation of the urinalysis apparatus 1, an operator inserts the container containing a subject's urine into the urinalysis apparatus 1. When the container is inserted inside, the control section 100 drives the conveyance mechanism 17, and conveys the container to the urinalysis mechanism 101. In the urinalysis mechanism 101, an amount of urine required for the urinalysis is sampled and analyzed. The urine that is not sampled but is left in the container is conveyed to the arm 4 via the conveyance mechanism 17.

The control section 100 controls the conveyance mechanism 17 to convey the container in which the urine is left to a gripping position under the arm 4, and is stopped thereby. The control section 100 controls the gripping portion 40 so that the gripping portion 40 is opened to be slightly larger than a diameter of the container. Next, the control section 100 controls the lifting mechanism 45 to lower the gripping portion 40. Furthermore, the control section 100 disposes the arm 4 at the gripping position and then controls the gripping portion 40 to close the gripping portion 40 and grip the container. Afterward, the control section 100 operates the lifting mechanism 45 again to lift up the container. When the container is gripped up by the gripping portion 40, the control section 100 operates and controls the lid 36 to open the lid 36 that closes an opening 35 of the rotor 30 as shown by arrow P4. The rotor 30 is constituted separately from the lid 36.

The control section 100 operates and controls the slide mechanism 18 to move the rotor 30 along the rail 13, thereby stopping the rotor under the arm 4 (a urine discarding position). When the opening 35 of the rotor 30 is stopped under the arm 4, the control section 100 operates and controls the gripping portion 40 of the arm 4 to rotate the gripped container to a necessary angle around the rotary shaft 46. Here, the necessary angle is an angle necessary for tilting the container to allow the urine in the container to flow to the rotor 30. As a result, the urine left in the container is discarded to the waste liquid tank 3.

The control section 100 allows the urine in the container to flow into the rotor 30, and then operates and controls the gripping portion 40 again to return the arm 4 to a position before the container is rotated. Afterward, the control section 100 operates and controls the slide mechanism 18 again to move the rotor 30 to a position of the lid 36, thereby stopping the rotor at the position (a container standby position). The control section 100 closes the lid 36. Note that the opening 35 is closed with the lid 36 to prevent the spread of an odor from the urine waste liquid.

When the rotor 30 is moved to the container standby position, a container insertion port 20 of the container collecting device 2 is moved to a position under the arm 4. In this state, the control section 100 operates and controls the gripping portion 40 to open the gripping portion 40. When the gripping portion 40 is opened, the container is dropped into the container collecting device 2.

Figure 3:
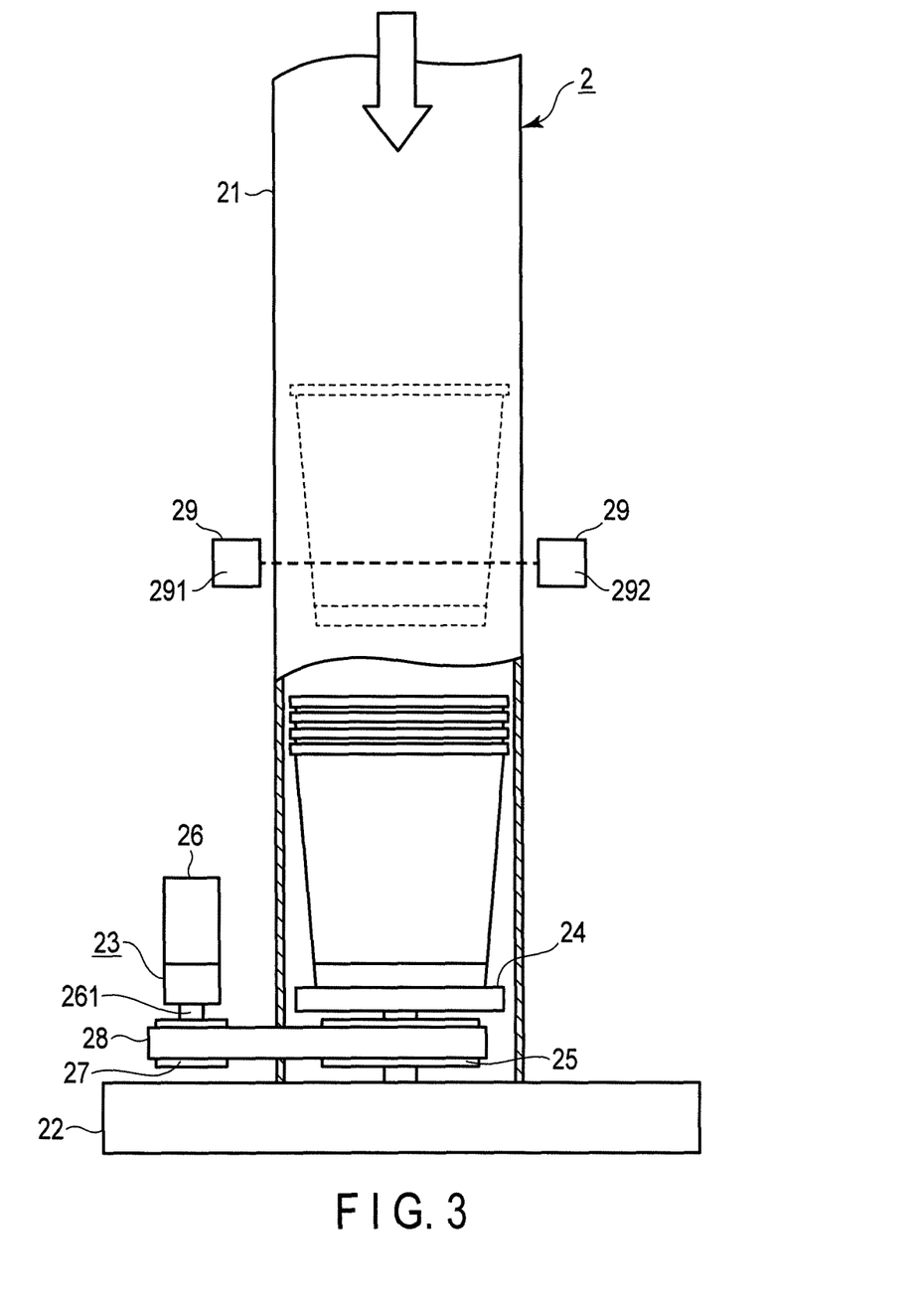
FIG. 3 is a schematic view of the container collecting device incorporated in the urinalysis apparatus of FIG. 1.

FIG. 3 is a schematic view of the container collecting device 2 related to the first embodiment.

The container collecting device 2 includes a guide cylinder 21 having an inner diameter slightly larger than the largest outer diameter of the container and extending in a gravity direction, a base member 22 disposed at a lower end of the guide cylinder 21, and an actuator 23 to move this container.

The guide cylinder 21 stabilizes a drop orientation of the container so that an axis of the container does not become oblique to the gravity direction when the container drops down. Therefore, the guide cylinder 21 is a cylindrical body having the inner diameter slightly larger than the largest outer diameter of the container for use, in accordance with the largest outer diameter thereof. Note that a shape of a cross section of the guide cylinder 21 is not limited to a circular shape. That is, the guide cylinder may have any sectional shape as long as the guide cylinder does not disturb the dropping of each container for use, but has a certain degree of drop stabilizing properties of the containers. Thus, the square pillar-shaped guide cylinder 21 having, for example, a cross section slightly larger than a quadrangular shape circumscribed to a circle of the largest outer diameter of the container, may be used.

In addition, the sensor 29 is disposed on an outer wall of the guide cylinder 21. The sensor 29 is usable as a so-called optical sensor. Specifically, when the optical axis extending from a light emitting portion 291 toward a light receiving portion 292 is blocked by the material or the liquid, a quantity of light to be received by the light receiving portion 292 changes. The sensor 29 detects the change of the quantity of the light to be received by the light receiving portion 292. When an open edge of the container blocks a space between the light emitting portion 291 and the light receiving portion 292, the sensor 29 detects that the quantity of the light to be received changes and the number of the containers reaches a predetermined number. For example, when the presumed number of the containers are stacked and a light source of the sensor 29 is blocked, a signal indicating the blocking is sent to the control section 100 to notify that it is time to collect the containers from the guide cylinder 21. In this case, the control section 100 stops the conveyance mechanism 17 to stop the conveyance of the containers until the containers are removed from the device.

There are no special restrictions on materials for use in the guide cylinder 21, but when hygienic concerns are taken into consideration, the guide cylinder is preferably formed by using a metal such as stainless steel or a resin such as an acrylic resin that is easily washable.

The base member 22 abuts on a lower end of the guide cylinder 21 to support the guide cylinder 21. In the first embodiment, a rotary seat 24 (a supporter) is disposed on an upper surface of the base member 22, and the container inserted into the guide is mounted on the rotary seat. That is, the rotary seat 24 is disposed coaxially with the guide cylinder 21 in the guide cylinder 21.

The actuator 23 includes the rotary seat 24 disposed coaxially with the guide cylinder 21, a first pulley 25 interposed between the base member 22 and the rotary seat 24 and fixed coaxially with the rotary seat 24, a motor 26 disposed on an outer side of the guide cylinder 21, a second pulley 27 attached to a rotary shaft 261 of the motor 26, and an endless belt 28 that transmits power of the motor 26 to the first pulley 25 via the second pulley 27.

Figure 4:
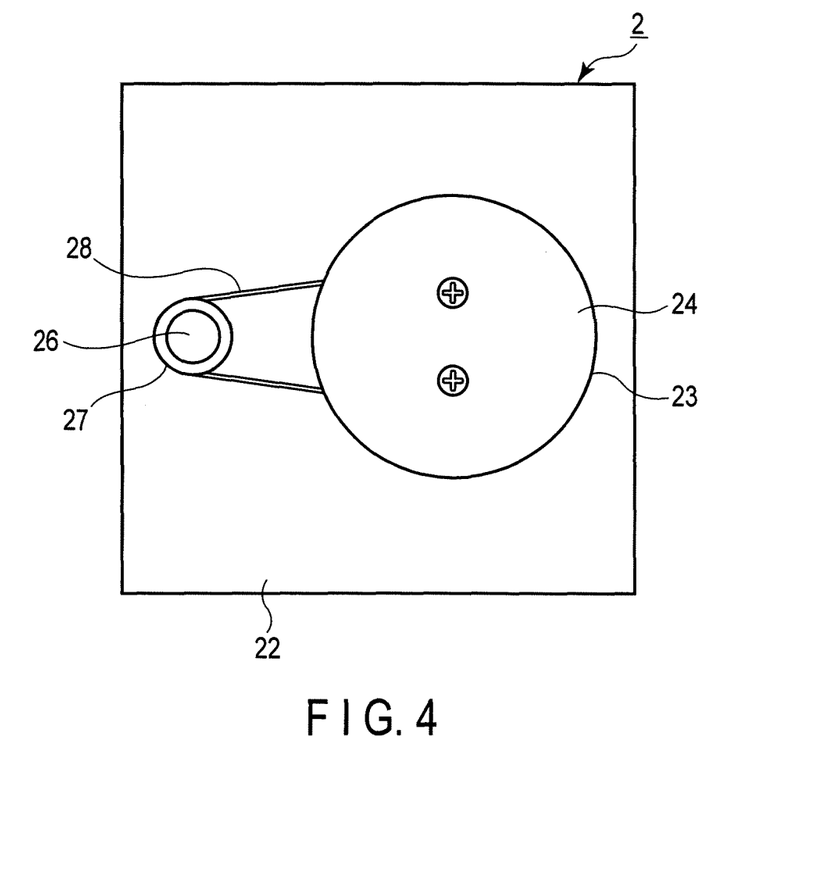
FIG. 4 is a plan view of the container collecting device of FIG. 3.

FIG. 4 is a plan view of the container collecting device 2 from which the guide cylinder 21 is removed. There are no special restrictions on a size of the rotary seat 24, but the rotary seat needs to be of sufficient size so that at least the bottom surface of the container is sufficiently mounted on the rotary seat. In the first embodiment, the rotary seat 24 is prepared by using a metal plate, but this material can be varied in consideration of friction between the rotary seat and the container during the rotation, weight, hygienic concerns, and the like. Additionally, in the first embodiment, the base member 22 is disposed separately from the rotary seat 24, but the base member 22 can be omitted.

Next, the operation of the container collecting device 2 of the first embodiment will be described.

When the gripping portion 40 is opened to drop the container into the container insertion port 20 of the guide cylinder 21, the control section 100 detects that the gripping portion 40 is opened in accordance with a signal from a sensor 41 disposed in the gripping portion 40. The control section 100 drives the motor 26 of the container collecting device 2 by use of this signal as a trigger to rotate the rotary seat 24 for about three seconds.

Next, a behavior of the dropped container will be described in detail.

First, a simple explanation will be given of the behavior of each container in the container collecting device in which the actuator 23 is not disposed.

Here, a container to be stacked is a container X, and the uppermost container already stacked is a container Y. Usually, the container X dropped from the arm 4 into the container insertion port 20 drops down along an axis of the guide cylinder 21. Furthermore, a bottom portion of the container X is inserted into an opening of the container Y, so that the container X is stacked on the container Y.

However, when the container X drops down in the guide cylinder 21, the container X sometimes drops down in a state where, for example, an axis of the container X is slightly oblique because a small amount of urine remains in the container X, or the container X is unfavorably separated from the gripping portion 40.

When the container X drops down in the guide cylinder 21 where the axis thereof is in an oblique state, an open edge of the container Y sometimes abuts on the bottom portion of the container X. When the bottom portion of the container X abuts on the open edge of the container Y, the container X that remains oblique stops on the open edge of the container Y. Therefore, the container X dropped in the guide cylinder 21 sometimes is not suitably stacked on the container Y.

Next, a simple explanation will be given of the behavior of the container in the container collecting device 2 of the present embodiment in which the actuator 23 is disposed.

When the gripping portion 40 is opened to drop the container X into the container insertion port 20, the control section 100 operates the actuator 23. Specifically, the control section 100 drives the motor 26 of the actuator 23 at this time. When the rotary seat 24 is rotated, the container Y disposed on the rotary seat 24 rotates. Thus, the container X abutting on the open edge of the container Y is moved in conjunction with the rotation of the container Y. Furthermore, due to this rotation of the rotary seat 24, the axis of the container X moves so as to extend along an axial direction of the guide cylinder 21, and the tilted orientation is corrected. As a result, the bottom portion of the container X is inserted into the opening of the container Y, and the container X is stacked on the container Y.

In the first embodiment, the control section 100 starts rotating the rotary seat 24 before the container X comes in contact with the container Y, but there are no special restrictions on timing when the rotary seat 24 rotates. For example, the control section 100 enables such setting that the container X completely drops down and then the rotary seat 24 rotates. Also, in this case the obliquely stacked container X is moved in conjunction with the rotation of the container Y rotated due to the rotation of the rotary seat 24. Therefore, the bottom portion of the container X is dropped into the open edge of the container Y, to stack the container on the container Y. In other words, the container is stacked on the container Y in a state where the axial direction of the container X matches the axial direction of the guide cylinder 21.

In the first embodiment, a rotation speed of the rotary seat 24 is set to 60 rpm. There are no special restrictions on the rotation speed and a rotation time of the rotary seat 24. That is, any speed may be set as long as movement is sufficiently given to move the obliquely stacked container into the open edge of the already stacked container so that the containers are stacked, and to prevent the urine left in the container from being spilled.

As described above, the predetermined number of the stacked containers are removed from a removal port (not shown) disposed in a part of the guide cylinder 21 and discarded by the operator.

As described above, according to the container collecting device 2 of the first embodiment, the containers are not obliquely stacked in the guide cylinder 21. Additionally, in the container collecting device 2 of the first embodiment, even when the containers are obliquely stacked, the orientation of each container can be arranged to stack the containers on one another by the abovementioned operation of the rotary seat 24. Therefore, the operator can securely stack the pre-determined number of the containers and then collect the containers. Therefore, the operator can collect a large number of containers at a time, and an operation of removing the containers can efficiently be carried out. Furthermore, the containers are suitably stacked, and thus the possibility that urine is spilled on the operator is lowered, which is hygienic. Needless to say, when the containers are discarded, the containers are not bulky in a garbage container.

Next, a container collecting device 5 relating to a second embodiment will be described.

A structure of a urinalysis apparatus 1 is similar to that of the first embodiment except that the container collecting device 2 is replaced with the container collecting device 5, and thus the description thereof is omitted.

Figure 5:
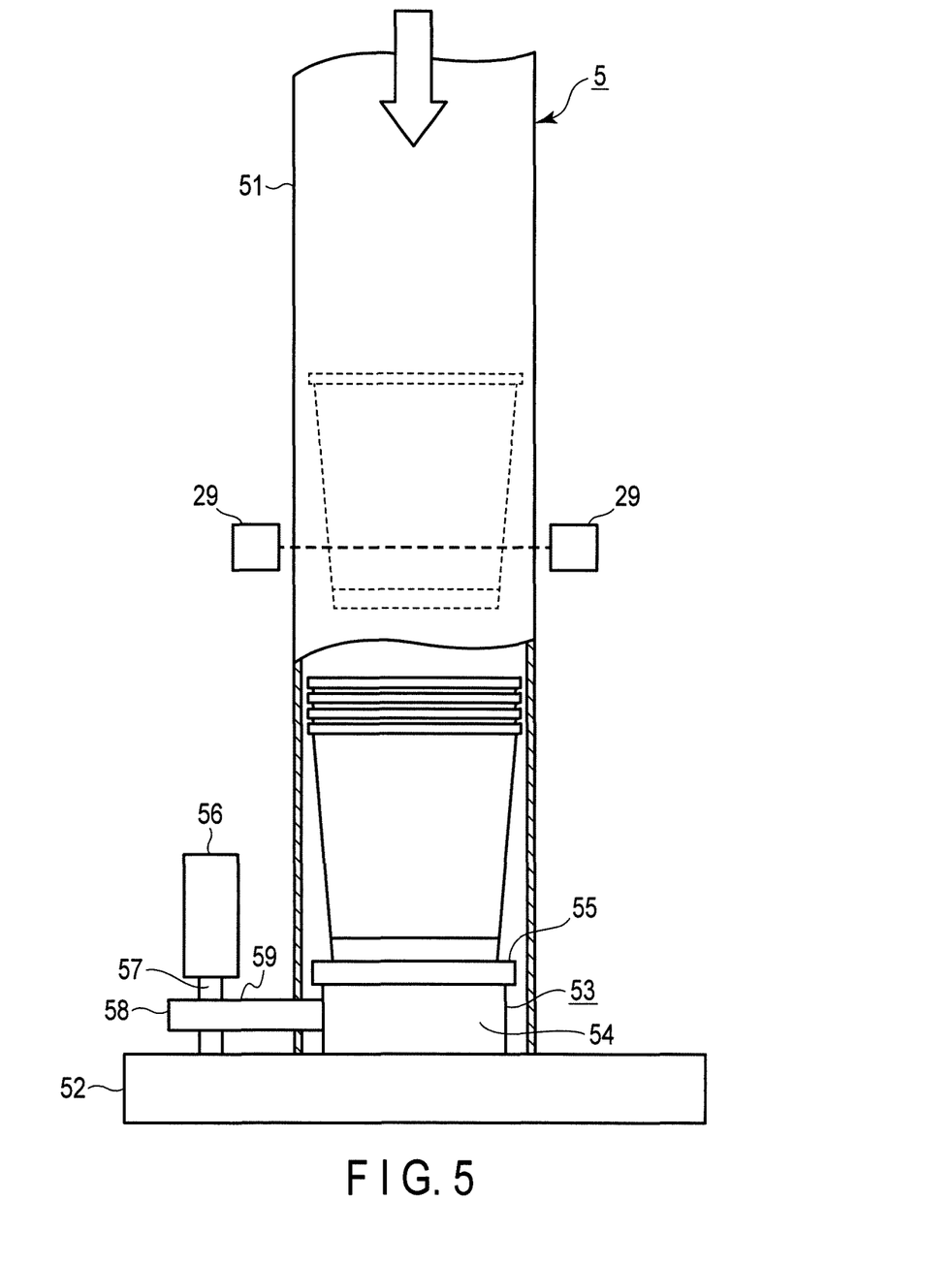
FIG. 5 is a schematic view of a container collecting device of a second embodiment.

As shown in FIG. 5, similarly to the container collecting device 2 of the first embodiment, the container collecting device 5 of the second embodiment has a guide cylinder 51 having an inner diameter larger than the largest outer diameter of each container to be received and extending in a gravity direction, a base member 52 that supports a lower end of the guide cylinder 51, an actuator 53 to move the container, and a sensor 29 that detects a time to collect the containers. Note that a container insertion port 50 is similar to that of the first embodiment shown in FIG. 1.

The guide cylinder 51 stabilizes the drop orientation of the container so that the axis does not become oblique when the container drops down.

The base member 52 is disposed at the lower end of the guide cylinder 51. In the second embodiment, a vibrator 54 is disposed on an upper surface of the base member 52, and on the vibrator, a seat 55 (a supporter) is disposed coaxially with the axis of the guide cylinder 51. The dropped container is stacked on the seat 55.

The actuator 53 of the second embodiment includes the vibrator 54, a motor 56, a rotary shaft 57, an endless belt 58, a pulley 59, and the seat 55. The seat 55 is fixed to the base member 52 via a support column (not shown). A rotor (not shown) is eccentrically rotatably attached to the support column. Furthermore, the endless belt 58 is wound around this rotor.

When the motor 56 is driven, a drive force is transmitted via the rotary shaft 57, the pulley 59, and the endless belt 58 to rotate the rotor. Therefore, the support column vibrates due to the rotation of the eccentrically disposed rotor. Due to this vibration, the seat 55 vibrates. An attaching position of the vibrator 54 is not limited to this position, as long as the obliquely stacked container may be moved by the vibration and may suitably be stacked on the container already dropped on the seat 55.

Figure 7:
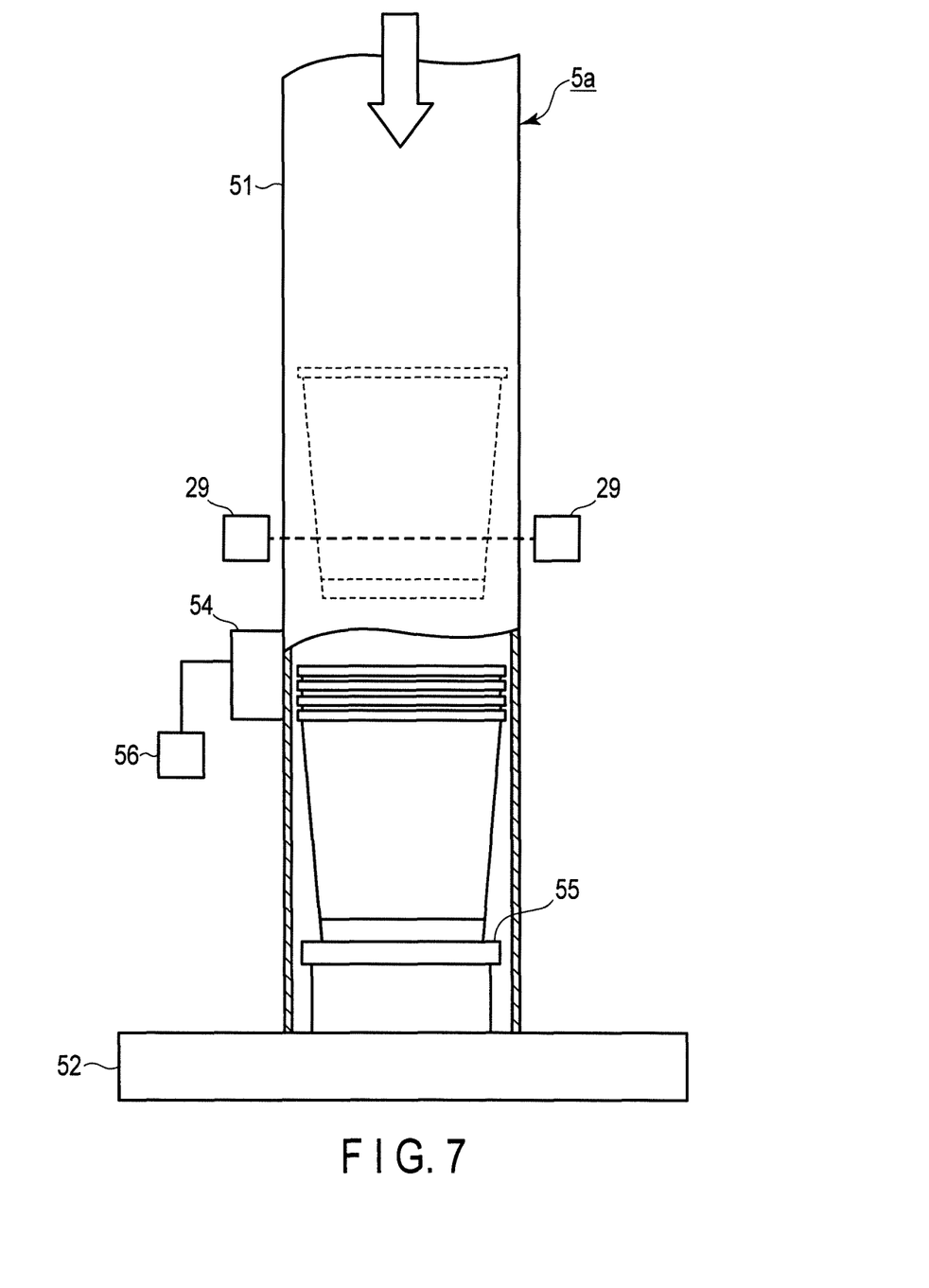
FIG. 7 is a schematic view showing a modification of the container collecting device of the second embodiment.

For example, as in a container collecting device 5a according to a modification of the second embodiment shown in FIG. 7, a vibrator 54 may be attached to an outer peripheral surface of a guide cylinder 51 and the vibrator 54 may be vibrated by a motor 56.

Next, an operation of the container collecting device 5 of the second embodiment will be described.

When a gripping portion 40 is opened to drop the container into the container insertion port 50 of the guide cylinder 51, a control section 100 detects that the gripping portion 40 is opened in accordance with a signal from a sensor 41 disposed in the gripping portion 40.

The control section 100 drives the motor 56 to vibrate the vibrator 54 for several seconds, on the basis of the signal from the sensor 41.

Next, the behavior of the container dropped in the container collecting device 5 will be described. Hereinafter, in the description, the dropped container is a container X, and the uppermost container already stacked in the guide cylinder 51 is a container Y.

The control section 100 drives the vibrator 54 at the same time when the container X drops down. A vibration generated by driving the vibrator 54 vibrates the seat 55 connected to the vibrator 54. This vibration is conducted to the container Y mounted on the seat 55. By this vibration, the container Y is vibrated. Furthermore, the vibration is conducted to the container X dropped from the container insertion port 50 to abut on the container Y. By this vibration, an abutment position between the container Y and the container X is moved.

Therefore, when the container X, for example, obliquely drops down to abut on an open edge of the container Y, the vibration of the container Y is also conducted to the container X, thereby gradually moving a tilt of the axis of the container X in a direction along the axis of the guide cylinder 51. Furthermore, when the tilt of the axis of the container X is beyond a certain point to release the abutment of a bottom portion of the container X on the open edge of the container Y, the container X is dropped and stacked into an opening of the container Y.

On the other hand, in the case of the container collecting device 5a, as shown in FIG. 7, a control section 100 drives the vibrator 54 at the same time when a container X drops down. A vibration generated by driving the vibrator 54 vibrates the guide cylinder 51 that abuts on the vibrator 54. This vibration is conducted to a container Y via a base member 52 and a seat 55. Furthermore, the vibration generated by driving the vibrator 54 is conducted to the container X dropped from a container insertion port 50 to abut on the guide cylinder 51 or the container Y. The vibration conducted to the container X moves an abutment position of the container Y on the container X and an abutment position of the guide cylinder 51 on the container X.

Therefore, when the container X, for example, obliquely drops down to allow an open edge of the container Y to abut on a bottom portion of the container X, the vibration applied from the vibrator 54 is also conducted to the container X, thereby gradually moving a tilt of the axis of the container X in a direction along the axis of the guide cylinder 51. Furthermore, when the tilt of the axis of the container X is beyond a certain point to release the abutment of the bottom portion of the container X on the open edge of the container Y, the container X is dropped and stacked into an opening of the container Y.

As described above, according to the container collecting device 5 of the second embodiment and the container collecting device 5a, the containers are not obliquely stacked in the guide cylinder 51. Additionally, in the container collecting device 5 of the second embodiment and the container collecting device 5a, even when the containers are obliquely stacked, the orientation of each container can be arranged to stack the containers on one another by the abovementioned operation of the vibrator 54. As a result, an operator can securely stack the pre-determined number of the containers and then collect the containers. Therefore, the operator can collect a large number of containers at a time, and an operation of removing the containers can efficiently be carried out. Furthermore, the containers are suitably stacked, and thus the possibility that urine is spilled on the operator is lowered, which is hygienic. Needless to say, when the containers are discarded, the containers are not bulky in a garbage box. Furthermore, in the container collecting device 5 of the second embodiment and the container collecting device 5a, the vibration is used as a power that corrects a position of each obliquely stacked container, and hence the urine or the like adhered to the inside of the container is not easily spilled, which is hygienic.

Next, a container collecting device 6 concerned with a third embodiment will be described.

A structure of a urinalysis apparatus 1 is similar to that of the first embodiment except that the container collecting device 2 is replaced with the container collecting device 6, and the description thereof is omitted.

Figure 6:
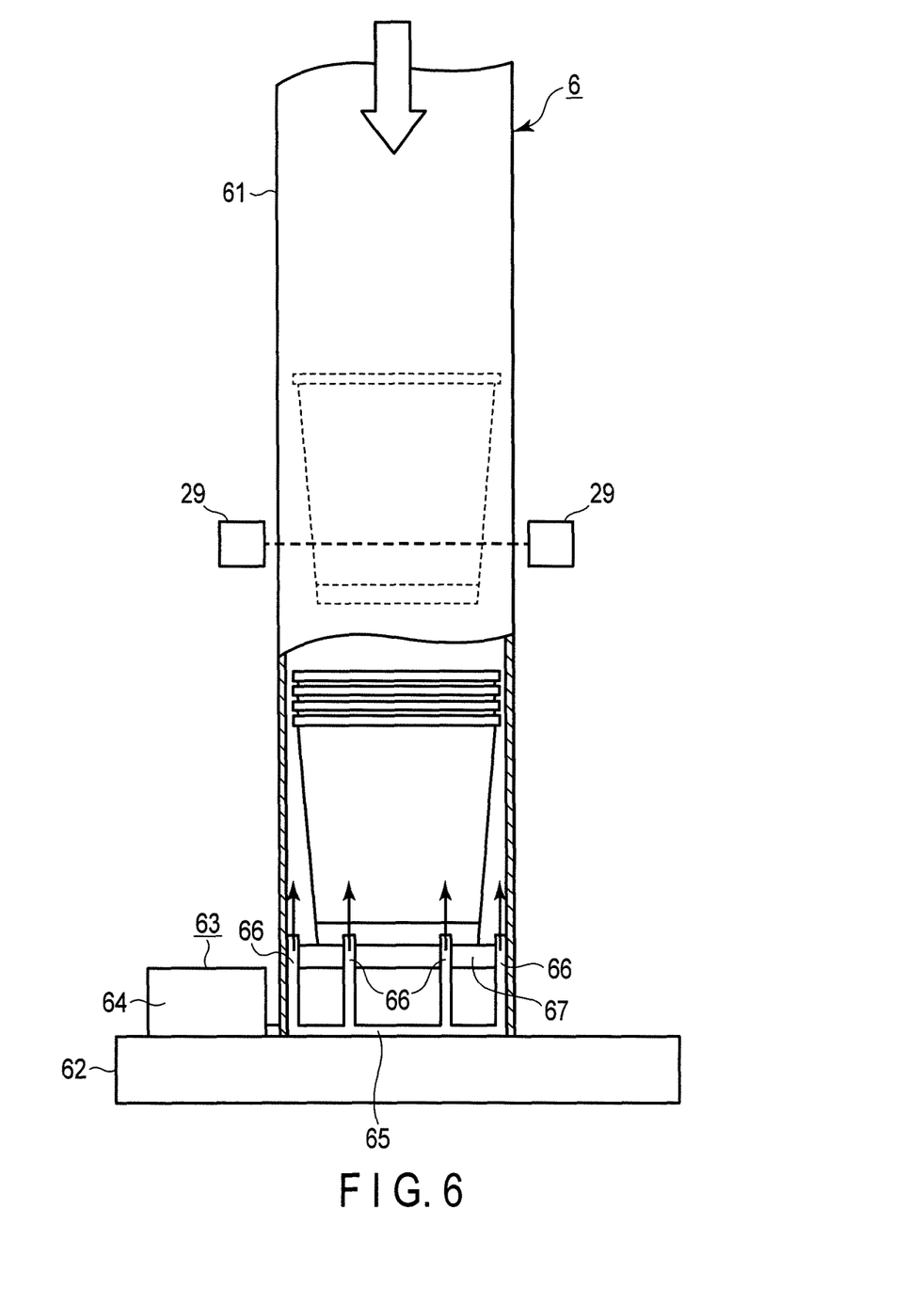
FIG. 6 is a schematic view of a container collecting device of a third embodiment.

As shown in FIG. 6, similarly to the container collecting device 2 of the first embodiment, the container collecting device 6 of the third embodiment has a guide cylinder 61 having an inner diameter larger than the largest outer diameter of each container to be received and extending in a gravity direction, a base member 62 that supports a lower end of the guide cylinder 61, an actuator 63 to move the container received in the guide cylinder 61, and a sensor 29 to detect a time to collect the containers. Note that a container insertion port 60 is similar to that of the first embodiment shown in FIG. 1.

The guide cylinder 61 stabilizes the drop orientation of the container so that the axis does not become oblique when the container drops down.

The base member 62 is disposed at the lower end of the guide cylinder 61. In the third embodiment, an air jetting device is used as the actuator 63 that moves the container. Specifically, the actuator 63 includes a compressor 64, an air channel 65 that feeds air into the guide cylinder 61, and nozzles 66 to jet the air. The air channel 65 having the nozzles 66 is connected to the compressor 64 disposed on an outer side of the guide cylinder 61.

At the lower end of the guide cylinder 61, a seat 67 (a supporter) is disposed away from the base member 62. Additionally, in an outer peripheral portion of the seat 67, six nozzles 66 are disposed to surround the seat 67. Here, there are no special restrictions on the number of the nozzles 66. However, for example, the number and positions of the nozzles to be disposed are sufficiently set so that the air to be jetted up from the seat 67 moves the containers. Therefore, the number and positions of the nozzles 66 are suitably designed in accordance with a thickness of the guide cylinder 61 for use, a size or a weight of each container, or the like.

Additionally, in the third embodiment, the nozzles 66 are set to an upper surface of the base member 62 so that distal ends of the nozzles 66 are directed in an axial direction of the guide cylinder 61, but a direction of the air jetted from the nozzles 66 can suitably be changed. For example, the nozzles 66 can be tilted as much as a predetermined angle to an axis of the guide cylinder 61 so that the air to be jetted is swirled and jetted along an inner peripheral surface of the guide cylinder 61.

Next, an operation of the container collecting device 6 of the third embodiment will be explained.

When a gripping portion 40 is opened to drop the container from the container insertion port 60 of the guide cylinder 61, a control section 100 detects that the gripping portion 40 is opened in accordance with a signal from a sensor 41 disposed in the gripping portion 40.

Next, the behavior of the container dropped into the container collecting device 6 will be explained. Hereinafter, in the description, the dropped container is a container X, and the uppermost container already stacked in the guide cylinder 61 is a container Y.

The control section 100 drives the compressor 64 at the same time when the container X drops down. As a result, in the inner peripheral surface of the guide cylinder 61, a flow of the air jetted from the nozzles 66 is generated. In this case, the container X dropped in the guide cylinder 61 stably drops down in a gravity direction along the axis of the guide cylinder 61 by the air that flows in a periphery. Due to this air, the axis of the container X is not obliquely tilted, but the container is dropped and stacked into the container Y.

In addition, if the container X is hung up on an open edge of the container Y in a state where the axis of the container X is tilted, the control section 100 jets the air from the nozzles 66 to move the container X. A contact point between a bottom portion of the container X and the open edge of the container Y is removed by the jetted air. As a result, the tilt of the axis of the container X moves in a direction along the axis of the guide cylinder 61. Furthermore, when the tilt of the axis of the container X is beyond a certain point to release the abutment of the bottom portion of the container X on the open edge of the container Y, the container X is dropped and stacked into an opening of the container Y.

As described above, according to the container collecting device 6 of the third embodiment, the containers are not obliquely stacked in the guide cylinder 61. Additionally, in the container collecting device 6 of the third embodiment, even when the containers are obliquely stacked, the orientations of the containers can be arranged by the abovementioned action of the air jetted from the actuator 63 so that the containers can be stacked on one another. Therefore, an operator can securely stack a pre-determined number of the containers and then collect the containers. Thus the operator can collect a large number of containers at a time, and an operation of removing the containers can efficiently be carried out. Furthermore, the containers are suitably stacked, and thus the possibility that urine is spilled on the operator is lowered, which is hygienic. Needless to say, when the containers are discarded, the containers are not bulky in a garbage box. Additionally, air is used, and thus even when urine remaining in the container is spilled by mistake, the device does not easily break down. In addition, the overall number of parts can be decreased.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

For example, in the present embodiment, the description has been given as to the container collecting device disposed in the urinalysis apparatus, but the container collecting device can be applied to objects such as disposable containers that are supplied in various vending machines for beverages, fast-food restaurants, and the like. Additionally, in the present embodiment, it is presumed that the containers for use have the same size, but may have slightly different sizes as long as the containers are stackable. Furthermore, in the present embodiment, the control section controls the driving of the actuator of any container collecting device, however, the container collecting device can, of course, be independently disposed. Additionally, various modifications are possible without departing from the gist of the present invention.

The invention claimed is:

1. A container collecting device which is adapted to stack and collect urinalysis containers each formed by closing a small-diameter side of a tapered cylinder and collected with the small-diameter side directed downward, the container collecting device comprising:
   a guide cylinder having an inner diameter larger than the largest outer diameter of the container and extending in a gravity direction; and
   an actuator including:
      a disk-shaped support configured to support an urinalysis container within the guide cylinder and configured to rotate the urinalysis container within the guide cylinder and relative to the guide cylinder, the disk-shaped support being located at a lower end of the guide cylinder and entirely inward of the lower end and being coaxial with the guide cylinder, and the disk-shaped support being configured to support a bottom surface of the urinalysis container;

a first pulley coaxial with the support;

a motor comprising a rotary shaft located outward of the guide cylinder;

a second pulley attached to the rotary shaft; and a belt wound around both the first pulley and the second pulley, wherein rotation of the first pulley via the motor, the second pulley and the belt rotates the disk-shaped support, and any urinalysis containers supported thereon, inside of and relative to the guide cylinder to stack and collect a predetermined amount of urinalysis containers in the guide cylinder and correct a tilted orientation of any of the urinalysis containers that may occur while forming the stack.

2. The container collecting device according to claim 1, further comprising:

a sensor that detects inserting the container into the guide cylinder; and a control section that drives the motor in accordance with a detection result of the sensor.

* * * * *